United States Patent [19]
Lundsgaard et al.

[11] Patent Number: 5,564,419
[45] Date of Patent: *Oct. 15, 1996

[54] METHOD OF PHOTOMETRIC IN VITRO DETERMINATION OF THE CONTENT OF OXYGEN IN A BLOOD SAMPLE

[75] Inventors: Finn C. Lundsgaard, Tastrup; Niels-Henrik Jensen, Farum; Willy Andersen, Espergærde, all of Denmark

[73] Assignee: Radiometer A/S, Bronshoj, Denmark

[*] Notice: The term of this patent shall not extend beyond the expiration date of Pat. No. 5,242,835.

[21] Appl. No.: 269,950

[22] Filed: Jun. 30, 1994

Related U.S. Application Data

[63] Continuation of Ser. No. 147,087, Nov. 3, 1993, abandoned, which is a continuation of Ser. No. 720,532, Jun. 21, 1991, abandoned, which is a continuation-in-part of Ser. No. 125,407, Nov. 25, 1987, abandoned.

[30] Foreign Application Priority Data

Dec. 22, 1988 [DK] Denmark ................... 7162/88
Dec. 21, 1989 [WO] WIPO .............. PCT/DK89/00300

[51] Int. Cl.$^6$ ........................................ A61B 5/00
[52] U.S. Cl. ................ 128/633; 128/637; 436/136
[58] Field of Search .................. 128/632–5, 637, 128/664–7; 356/39–41; 604/93, 198; 436/136, 138

[56] References Cited

U.S. PATENT DOCUMENTS

| 3,926,521 | 12/1975 | Ginzel . | |
|---|---|---|---|
| 4,426,451 | 1/1984 | Columbus . | |
| 4,454,229 | 6/1984 | Zander et al. . | |
| 4,496,344 | 1/1985 | Kamstra . | |
| 4,645,744 | 2/1987 | Charlton et al. . | |
| 4,654,197 | 3/1987 | Lilja . | |
| 4,657,756 | 4/1987 | Marsoner . | |
| 4,703,182 | 10/1987 | Kroneis . | |
| 4,737,144 | 4/1988 | Choksi . | |
| 4,775,514 | 10/1988 | Barnikol . | |
| 4,781,701 | 11/1988 | Geprags . | |
| 4,810,090 | 3/1989 | Boucher et al. . | |
| 4,873,993 | 10/1989 | Meserol . | |
| 4,929,426 | 5/1990 | Bodai . | |
| 4,940,945 | 7/1990 | Littlejohn . | |
| 5,025,798 | 6/1991 | Schindele . | |
| 5,029,583 | 7/1991 | Meserol et al. | 128/633 |
| 5,046,496 | 9/1991 | Betts . | |
| 5,064,618 | 11/1991 | Baker . | |
| 5,066,859 | 11/1991 | Karker . | |
| 5,080,865 | 1/1992 | Leiner et al. . | |
| 5,120,510 | 6/1992 | Gourley et al. | 422/82.07 |
| 5,127,077 | 6/1992 | Iyer et al. | 128/634 |
| 5,242,835 | 9/1993 | Jensen | 436/136 |

Primary Examiner—Angela D. Sykes
Attorney, Agent, or Firm—Bryan Cave LLP

[57] ABSTRACT

In a method of photometric in vitro determination of the content of oxygen in a blood sample, a blood sample is transferred directly from an in vivo locality to an at least partially transparent sample container of a sampling device. The sample container has a measuring chamber containing a luminophor, the luminescence of which is quenched in the presence of oxygen. The luminophor is excited by irradiation with radiation from a radiation source. The luminescence emitted by the excited luminophor is detected by a radiation detector and the oxygen content determined on the basis of the radiation detected by the radiation detector. A sampling device and a system for photometric in vitro determination of oxygen in a blood sample are also described.

17 Claims, 6 Drawing Sheets

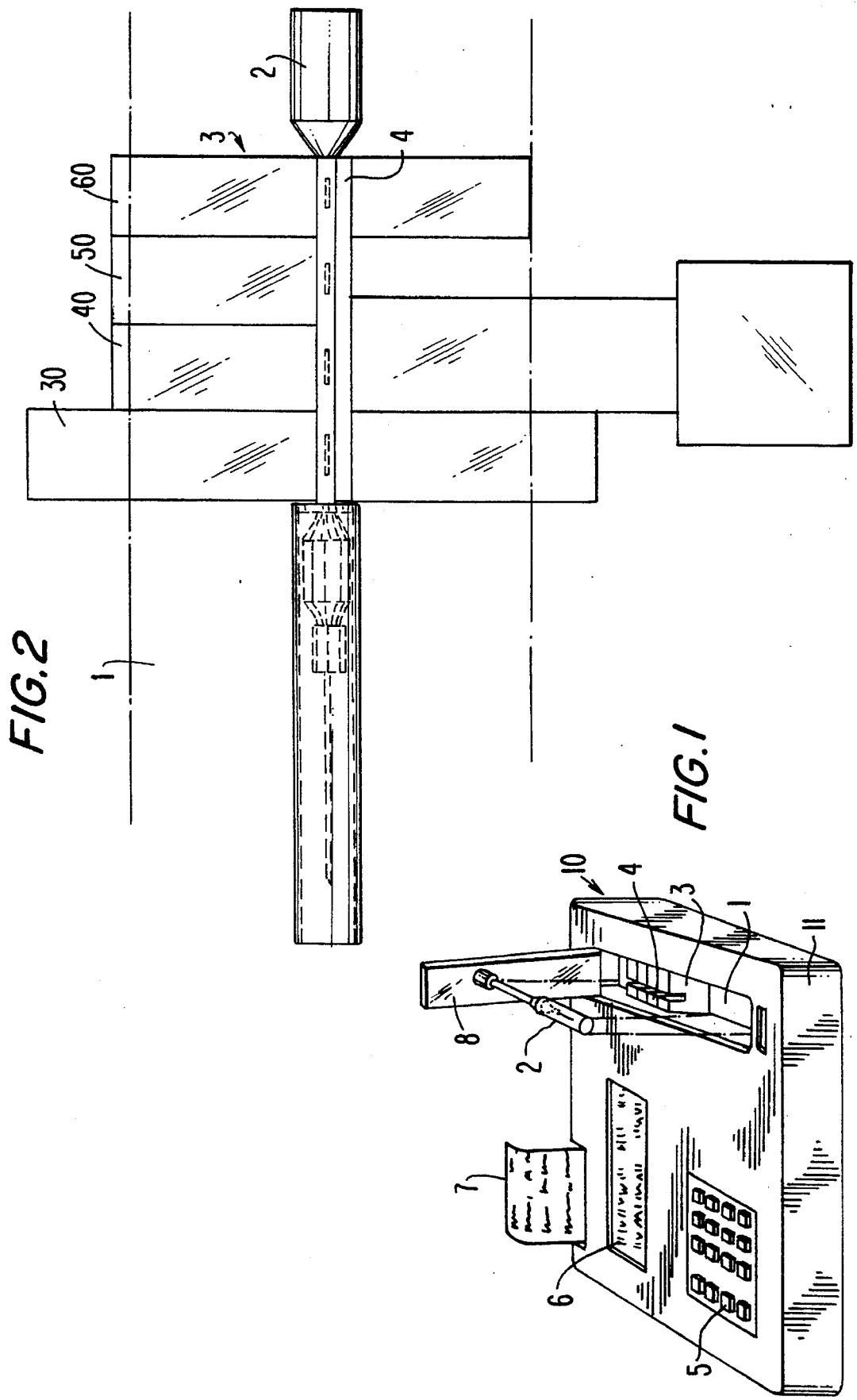

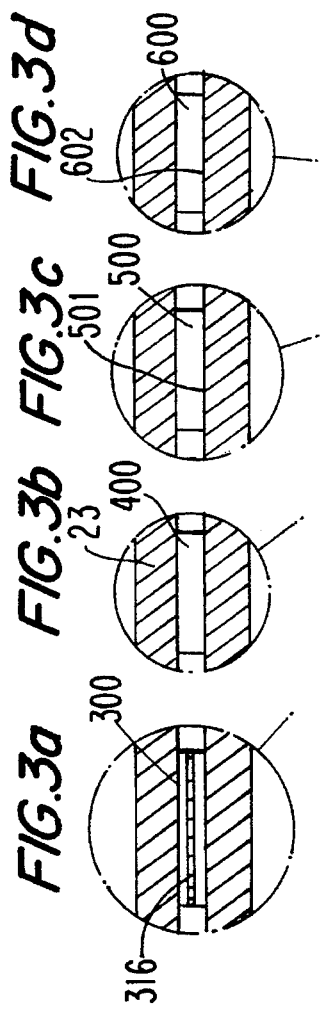
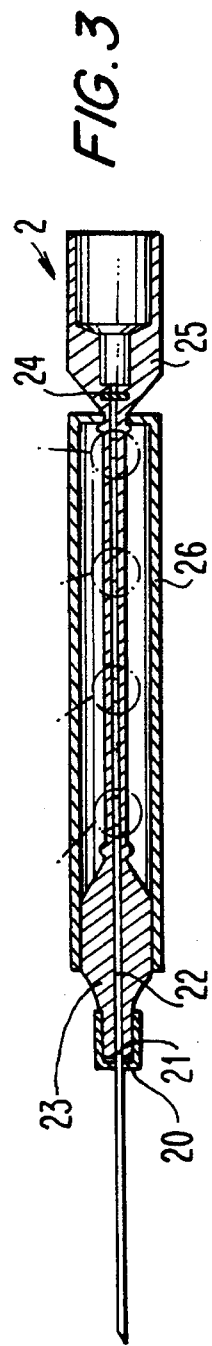
FIG.3
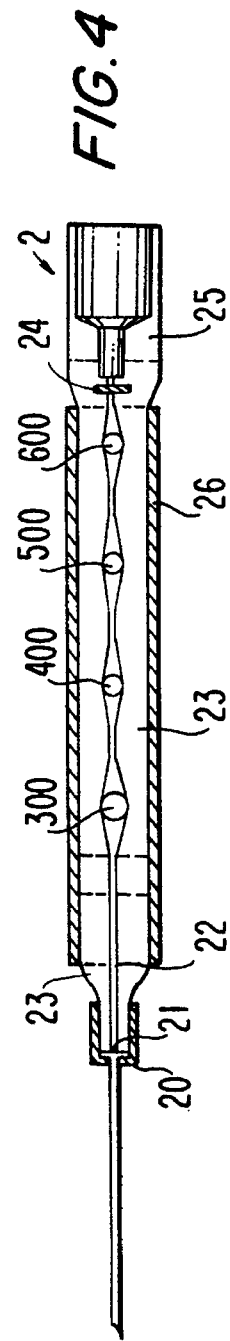
FIG.4
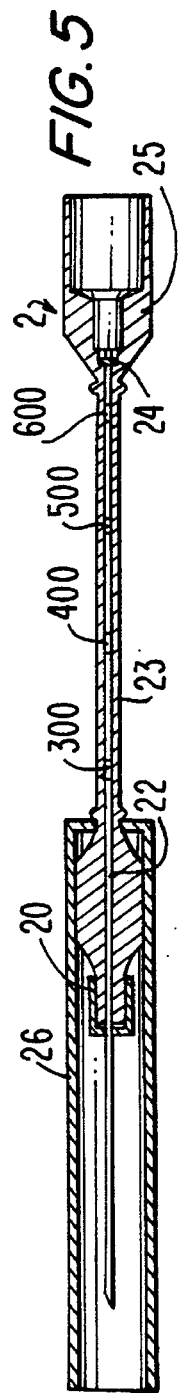
FIG.5

METHOD OF PHOTOMETRIC IN VITRO DETERMINATION OF THE CONTENT OF OXYGEN IN A BLOOD SAMPLE

This is a continuation of Ser. No. 08/147,087 filed Nov. 3, 1993, now abandoned; which is a continuation of Ser. No. 07/720,532 filed Jun. 21, 1991, now abandoned; and which is a continuation-in-part of Ser. No. 125,407 filed Nov. 25, 1987, now abandoned.

FIELD OF THE INVENTION

The present invention relates to a method of photometric in vitro determination of the content of oxygen in a blood sample by means of luminescence quenching, utilizing a luminophor, the luminescence of which is quenched in the presence of oxygen, with the content of the oxygen determined on the basis of a luminescence characteristic of the luminescence emitted from the excited luminophor.

BACKGROUND OF THE INVENTION

It has been known for some years to determine the content of molecular oxygen in a sample by using optical methods based on luminescence quenching. In general, these methods comprise measuring the luminescence intensity and/or the luminescence lifetime of a suitable luminophor, the luminophor being in contact with an oxygen-containing sample and being exposed to illumination. The basic feature of luminescence quenching is the deactivation of the luminescing excited electronic state of the luminophor taking place on collision with oxygen molecules. As the average number of luminophor molecules in the excited electronic state is reduced by the interaction with the oxygen molecules, the luminescence intensity and the excited state lifetime of the luminophor are reduced. The magnitude of the reduction is connected with the number of oxygen molecules in contact with the luminophor through the Stern-Volmer equation $$M^\circ/M = 1 + K_{sv} \cdot [O_2]$$

see e.g. IUPAC Commission on Photochemistry, and "Glossary of Terms used in Photochemistry, part III", EPA Newsletter, July 1986. $M^\circ$ and $M$ of the above equation designate the luminescence intensity or the excited state lifetime of the luminophor in the absence and presence of oxygen, respectively. $[O_2]$ designates the concentrations of molecular oxygen corresponding to the M-value measured. $K_{sv}$ is the so-called Stern-Volmer constant explained in the above reference. By using this equation and correlating it to samples of known oxygen content, it is possible to determine the oxygen content of a sample. Photometric determination of the oxygen content in blood or other media by the so-called luminescence quenching is known from i.a.:

Bacon, J. R and Demas, J. N., "Determination of oxygen concentrations by luminescence quenching of a polymer immobilized transition-metal complex", Anal. Chem., 59, 1987, 2780–2785, Longmuir, I. S. and Knopp, J. A., "Measurement of tissue oxygen with a fluorescent probe", Journal of Applied Physiology, 41, 1976, 598–602, Waughan, W. M. and Weber, G., "Oxygen quenching of pyrenebutyric acid fluorescence in water. A dynamic probe of the microenvironment", Biochemistry, 9(3), 1970, 464–473, Bergman, I., Nature 218, 1958, 376, Stevens in the specification of U.S. Pat. No. 3,612,866, Stanley in the specification of U.S. Pat. No. 3,725,658, Bacon, J. R. and Demas, J. N. in the specification of British patent application GB 2132348, Peterson et al. in the specification of U.S. Pat. No. 4,476,870, Buckles, R. G. in the specification of U.S. Pat. No. 4,399,099, Hirschfeld, T. in the specification of U.S. Pat. No. 4,542,987, Dukes et al., in the specification of U.S. Pat. No. 4,716,363, Lübbers et al. in the specification of U.S. Reissue Pat. No. 31,879, Kahil et al. in the specification of International patent application WO 87/0023, Murray, R. C., Jr. and Lefkowitz, S. M. in the specification of European patent application EP 190829, Murray, R. C., Jr. and Lefkowitz, S. M. in the specification of European patent application EP 190830, and Hesse, H. C. in the specification of East German patent DD 106086.

Determination of the intraarterial values of the blood gas parameters pH, oxygen ($O_2$) and carbon dioxide ($CO_2$) by means of a fluorescence based measuring system is known from Miller et al,. "Performance of an in-vivo, continuous blood-gas monitor with disposable probe", Clin. Chem. 33(9), 1987, 1538–1542.

Extracorporeal determination of all three parameters by means of another fluorescence based measuring system Gas-STAT™, produced by Cardiovascular Devices Inc., USA, is finally described i.a. in brochures concerning this system and in the article by Clark, C. L., "Early clinical experience with Gas-STAT", J. Extracorporeal Technol., 18(3), 1986, 185–189. The determination of the blood gas parameters proceeds continuously in the GAS-STAT™ system. Inside a cuvette, which is inserted in the extracorporeal circulation established at a cardiac operation, fluorescence based sensors are placed. Via optical fibers excitation radiation is provided and emitted fluorescence radiation is taken away. The intensity of the latter depends of the concentration on the matter measured by the relevant sensor.

None of these publications relating to photometric analysis of oxygen describes an in vitro method for determination of oxygen in discrete samples and based on simple sample handling principles.

In vitro determination of oxygen in a blood sample has so far mostly been performed by means of blood gas analyzers as, e.g. the blood gas analyzers produced and sold by Radiometer A/S, Copenhagen, under the name ABL Acid-Base Laboratory.

These analyzers are mechanically complex, since the blood samples i.a. have to pass through the very fine fluid conduits of the analyzer, in which conduits electrochemical sensors are built-in. Blockage in the conduits or coatings on the active surfaces of the sensors can easily occur and interfere in or destroy a measurement.

On account of these circumstances the existing equipment requires frequent maintainance performed by specially trained personnel, and the equipment will normally be placed in a laboratory situated at a certain distance from the patient. A response period of more than 10 min. and normally up to half an hour from the time of the sampling to the moment of obtaining the analytical result is therefore not unusual. Beyond that the waiting period can be unfortunate in connection with the medical treatment of the patient, the relatively long waiting period also has the consequence that the sample is to be kept cooled down to app. 0° C. This is due to the fact that at higher temperatures the metabolic processes of the blood will cause changes in the blood gas parameters during the relevant periods.

Another disadvantage of the existing equipment is that there exists a certain risk for the operator to get in touch with sample residues with the health risks this may imply in the form of transfer of infections, etc.

British patent application GB 2 025 065 (Meiattini, F. et. al.) a mechanically simpler in vitro system comprising a plunger syringe for withdrawal of a blood sample. The blood sample is analysed by means of sensors incorporated in the syringe plunger is thereby avoiding transfer of the sample to a separate measuring chamber.

The sensors are adapted for connection with an analyzer via conductors for registering, processing, and printing out analytical data. The specific sensors described in the specification of the said British patent application GB 2 025 065 are electrochemical sensors for blood gases and blood electrolytes.

It shall finally be mentioned that the technological basis also comprises other clinical chemistry analyzers consisting of a combination of disposable components, which are only used for one single analysis operation and only get in touch with one single sample, and an analyzing section adapted for receiving the sample-containing, disposable device and containing the additional components necessary for accomplishing a clinical chemical analysis. Special blood gas analyzers are, however, not known among these. Apart from analyzers of the type disclosed in the abovementioned GB 2025065 wherein the sensors are electrochemical sensors, there are no known in vitro oxygen analysers based on disposable components.

SUMMARY OF THE INVENTION

The object of the invention is to provide an in vitro method for determination of the content of oxygen in a blood sample, the method being more appropriate for the user in that there is obtained both a more simple and less risky sample handling and a more simple maintenance of the oxygen analyzer utilized in practising the method. This is achieved by the method according to the invention, comprising transferring a blood sample from an in vivo locality to the sample container of a sampling device, the sample container having a measuring chamber with an at least locally transparent wall part and containing a luminophor; breaking the connection between the sampling device and the in vivo locality after filling the sample container with the blood sample; bringing the measuring chamber into optical communication with an optical system comprising a radiation source and a radiation detector; exciting the luminophor within the measuring chamber by irradiation with radiation from the radiation source; and determining the luminescence characteristic of the luminescence emitted from the luminophor based on the luminescence detected at the radiation detector.

BRIEF DESCRIPTION OF THE DRAWINGS

FIG. 1 is a perspective view of a preferred embodiment of an analyzer and a sampling device according to the invention, which together constitute a system for photometric in vitro determination of the content of oxygen in a blood sample;

FIG. 2 is an enlarged schematic view from above of the sample container station of the analyzer with the sampling device;

FIG. 3, 3a, 3b, 3c and 3d, FIG. 4 and FIG. 5 are views of a preferred embodiment of a sampling device according to the invention;

DETAILED DESCRIPTION OF THE INVENTION

Figure 6:
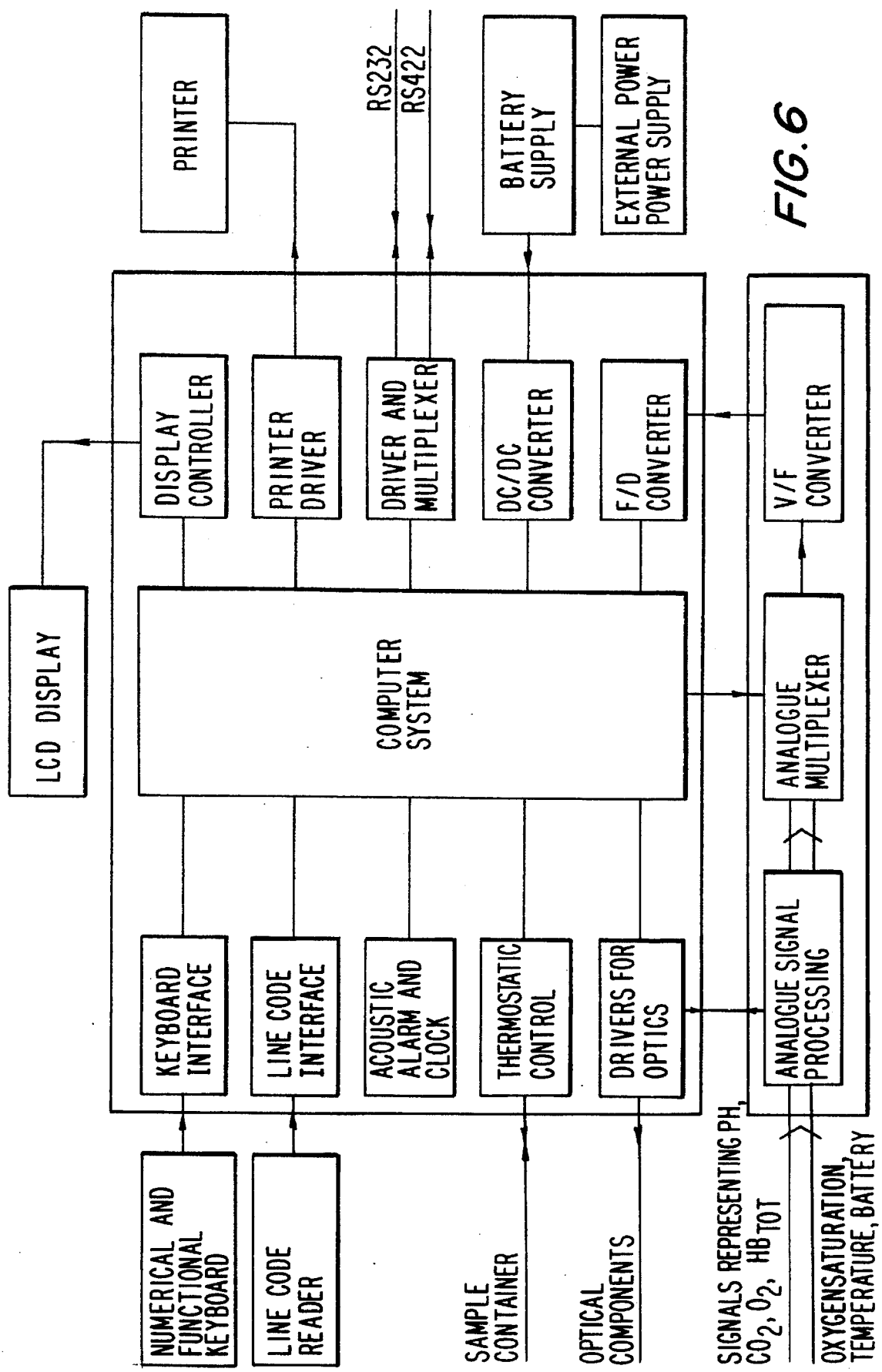
FIG. 6 is an electric block diagram of the analyzer shown in FIG. 1.

"In vivo locality" denotes in the present context a locality being in direct connection with the blood circulation or being a locality in the blood circulation itself. Sampling by arterial puncture, whereby the blood sample is transferred from the artery to the sample container by a thin needle, as well as via an arterial catheter or via capillary puncture are sampling methodologies, in which the blood sample is transferred directly from an in vivo locality to a sample container.

"Luminescence characteristic" as used herein refer to any way of characterizing or measuring luminescence. Conventionally, luminescence is characterized by the luminescence intensity, which is to be understood in its broadest sense, i.e. the magnitude of the luminescence signal obtained during continuous excitation or, the integrated value of the time-dependent luminescence signal obtained upon pulsed excitation, or the first derivative of the decaying part of said time-dependent luminescence signal. However, other ways of expressing the luminescence characteristic such as the phase shift between the luminescence signal and a modulated oxygen excitation signal are to be considered to be within the definition of the term "luminescence characteristic".

Preferably, the luminophor is selected among the luminophors disclosed in the above-mentioned publications or in applicant's international patent application WO 89/04476.

Preferred luminophors are palladiumporphyrins, e.g. palladium(II)-tetraphenylporphyrin (PdTPP) or palladium (II)-tetra-(pentafluorophenyl)-porphyrin (PdTFPP).

Another fluorophor which is expected to be suitable is arylsubstituted tetrabenzoporphyrin. These luminophors are especially suited for blood measurements when immobilized in a polymer matrix of hard PVC, i.e. PVC substantially without any content of plasticizer.

It has now been found that a sampling device of the type wherein the luminophor is a palladiumporphyrin embedded in a polymer matrix of hard PVC has an excellent storage stability of several months. Due to this stability ($K_{sv}$ is unchanged) it is possible to avoid calibration of such devices by the user.

The above mentioned less risky sample handling is i.a. a consequence of the possibility of removing the practically closed sample container with its content of blood sample after the termination of the analysis procedure. This removal is a sanitarily appropriate arrangement, which—in relation to the methods, by which a sample is transferred from the sampling container to an analyzer and from there to a waste container—reduces the risk for the user to get in touch with possibly infected sample residues.

The actual transfer of the blood sample from the sampling device to the measuring apparatus according to the prior art is a not unessential source of error within blood gas analysis. This source of error is eliminated by the method according to the present invention.

Apart from the more simple and less risky sample handling and the reduced maintenance of the analyzer obtained by the method according to the present invention, there is also in other ways obtained a simplified analysis procedure compared to the current oxygen analysis methodology.

The current methodology using equipment based on electrochemical sensors normally involves a relatively frequent calibration of the sensors. By traditional blood gas analyzers calibration routines are prescribed, whereby the sensors with an interval of 1 to 2 hours are contacted by a liquid or gaseous calibration medium with a specific content of the relevant parameters. The calibration medium is discarded after use and the operator therefore has to secure the presence of the necessary calibration medium. By the realization of the method according to the invention this calibration medium consuming calibration process can—at least as far as concerns preferred embodiments—be avoided.

Locally, the sample container has to communicate optically with the radiation source and the radiation detector, both of which preferably are located outside the sample container, and it therefore has to be made of a material which is transparent for the relevant radiation at least in the areas communicating with the radiation source and the radiation detector. The material also has to provide the sample container with a sufficient diffusion tightness for oxygen, which means that the content of oxygen may not change substantially during the time normally passing from the sampling to the moment of the analysis.

The sample container may include one measuring chamber or several measuring chambers arranged in series or in parallel. The sample container is preferably made of an injection moldable polymeric base material. A suitable base material is polyethylene terephtalate which e.g. is sold under the trade name Arnite™ from AKZO, Arnhem, Holland.

Preferably, the wall parts of the measuring chamber are made of a polymer material with low oxygen permeability and suitable transmission characteristics for radiation at the wavelengths relevant to the oxygen determination (as further disclosed at another page). A suitable material is an ethylene vinylalcohol copolymer of the type EVAL-E™ which is sold by Kuraray Co., Osaka, Japan. Alternatively, the wall parts of the measuring chamber may be made of glass or combinations of glass and polymer.

In a preferred embodiment the method is characterized in, that the optical communication is provided by placing the sample container in a sample container station in an analyzer.

Alternatively, the optical communication can be established by one or several cables, which via contact elements to the sample container and optical fibers establish optical communication between the optical system and the sample container.

In the case where the blood sample is provided by capillary puncture, the use of a sample container with a dimension sufficiently small for the sample container to be filled by capillary effect is preferred.

In the case where a sample of arterial blood is desired, the use of a sample container with an inlet located in a coupling means, preferably a Luer cone, for coupling the sample container to a needle or a catheter is preferred.

In the case where the sampling of the blood sample is performed by use of a needle coupled to the sample container, it is especially advantageous to provide the sample container with a needle protecting means integral therewith, preferably a jacket movable in the axial direction of the sample container between a first position, wherein the jacket exposes the point of the needle, and a second position, wherein the jacket surrounds the point of the needle.

With this preferred embodiment of the sample container it is possible to obtain sufficient security for the user against being injured by the needle just by displacing the jacket into the second position after the sampling. The user is thus not in risk of getting in touch either with the needle carrying part itself or with the immediately surrounding area during removal or application of a protecting means.

Alternatively the needle protecting means can be an elongated gully-shaped element pivotally mounted around an axis located near the inlet of the sample container. During sampling the needle protecting means surround the sample container, while the needle is exposed. By 180° rotation around the axis the needle protecting means are brought to surround the needle, while the sample container is exposed.

The invention also relates to a sampling device with a sample container which, apart from an inlet opening, is essentially sealed, and a measuring chamber with an at least locally transparent wall part containing a luminophor, the luminescence of which is quenched in the presence of oxygen. Preferred embodiments of the sampling device according to the invention have the characteristic following features. The sample container may have a dimension sufficiently small for the sample container to be filled by capillary effect. The sample container may have an inlet located in a coupling means, preferably a Luer cone, for coupling the sample container to an element, preferably a needle or a catheter, adapted for transferring the blood sample from the in vivo locality to the sample container. The sampling device may comprise an elongate sample container with a needle coupled thereto, the sample container having a jacket movable in the axial direction of the sample container between a first position where the jacket exposes the needle and a second position where the jacket surrounds the needle.

The luminophor of the sampling device may be immobilized at an inner surface of the wall part of the measuring chamber. The luminophor may be immobilized in a polymer matrix which preferably forms a coating on an inner surface of the wall part of the measuring chamber. The polymer matrix may be cellulose acetate, polyurethane, polycarbonate silicone copolymer, or hard polyvinyl chloride. The luminophor is a porphyrin compound which, when embedded in the particular polymer matrix, provides a luminescence characteristic of a sufficient size variation allowing the oxygen partial pressure to be determined as long as the ambient oxygen partial pressure varies within the physiological range, i.e., with the range of up to approximately 800 mmHg, preferably up to mmHg, more preferably up to 150 mmHg, and most preferably up to 120 mmHg. In another preferred embodiment of the sampling device, the polymer matrix is hard polyvinyl chloride and the luminophor is a palladiumporphyrin, e.g., palladium(II)-tetraphenyl porphyrin (PdTPP) or palladium(II)-tetra-(pentafluorophenyl)-porphyrin (PdTFPP).

The sampling device according to the inventions has a sample container with an inlet opening and apart from the inlet opening the sample container is an essentially sealed container. In the present context it is hereby understood that no transport of blood sample into or from the sample container can take place otherwise than through the inlet opening. However, the sample container may comprise vent openings or the like.

Besides, the invention relates to a system for photometric in vitro determinations of the content of oxygen in a blood sample. The system according to the invention comprises a sampling device with a sample container which, apart from an inlet opening, is essentially sealed, and a measuring chamber with an at least locally transparent wall part containing a luminophor, the luminescence of which is quenched in the presence of oxygen; and an analyzer with an optical system comprising a radiation source and a radiation detector, and a means for providing optical communication.

In a preferred embodiment the analyzer comprises data processing means for processing the registered radiation data for deriving the content of oxygen from these. Alternatively the analyzer is adapted for connection to a separate data processing unit.

In a further preferred embodiment of the system according to the invention the analyzer comprises means for displaying the oxygen content or any possible parameters derived from this. Alternatively, the analyzer is adapted for connection with means such as, e.g. a data screen, a display, a printer, or a plotter.

The invention will now be explained in the following with reference to the drawings and the subsequent examples.

The analysis system shown in FIG. 1 and generally designated 10 is a compact portable "stand-alone" system, which is suited for decentral use, i.e. use outside a regular laboratory environment, e.g. in an operating room or at an intensive ward. The analysis system 10 comprises a sampling device 2 for disposable use and used in connection with an analyzer 11. The sampling device 2 is more explicitly described in connection with the description of FIG. 3–5 below. The sampling device 2 and the analyzer 11 are adapted to interact in the way that the analyzer 11 has a sample container station 1 with an optical section 3 adapted for receiving the sampling device 2 or at least the sample container thereof, so that the optical communication between the sample container and the optical components of the optical unit 3, Which is necessary for photometric analysis, is obtained.

The sample container station 1 can be closed by a cover 8, which is closed after placing the sampling device 2 in the station. By closing the cover 8 different mechanisms are activated, e.g. a not shown clamping mechanism, which secures the sampling device 2 in the optical section 3 and at the same time thermostatically controls the sample container to a desired temperature, preferably app. 37° C.

Closing the cover 8 further results in a signal being sent to the controlling unit of the analyzer and indicating the start of an analysis procedure. An operator can control the operation of the analyzer by means of a keyboard 5 and a display 6. The analyzer 11 preferably also comprises a printer, which can produce an outprint 7 of i.a. the analysis results obtained by the analyzer.

After placing the sampling device 2 in the sample container station 1 and closing the cover 8 of this, the optical components comprising of radiation sources and radiation detectors are activated, whereupon the analyzer 11 calculates one or several blood gas parameters on the basis of the signals from the radiation detectors. The result of the calculations is displayed on the display 6 and is printed on the paper outprint 7 by the printer. When the calculations are terminated and the results displayed and/or printed out the cover 8 is opened and the sampling device 2 is displaced from the sample container station 1 and disposed of.

In a larger scale FIG. 2 shows a partially schematic section of the sample container station 1 viewed from above.

As shown the optical section 3 comprises four optical units 30, 40, 50, and 60 each adapted for determination of its respective blood parameter. The sampling device is placed in a slot 4 in the optical section 3.

The optical unit 30 contains the optical components necessary for photometric determination of pH. The optical unit 40 contains the optical components necessary for photometric determination of carbon dioxide. The optical unit 50 contains the optical components necessary for photometric determination of oxygen and finally the optical unit 60 contains the optical components necessary for photometric determination of hemoglobin. Even though the analyzer 11 is shown containing four optical units it can in principle contain an arbitrary number and/or an arbitrary combination of units beyond the unit for use in the determination of oxygen.

FIG. 3 shows a longitudinal section of the sampling device 2 and four segments of the sampling device are illustrated in a larger scale in FIGS. 3a, 3b, 3c and 3d. The sample container comprises a body 23, which at least in specified areas is made of a material transparent for the relevant radiation. The body 23 has a continuous conduit 22 locally extended for forming measuring chambers 300, 400, 500, and 600. During a course of measurement the actual blood sample fills the conduit 22 from its inlet aperture 21 to a hydrophobic filter 24 placed behind the measuring chambers. The section of the body 23 surrounding the inlet aperture is provided with a Luer cone and is therefore suitable for being mounted with a needle 20 of the type normally used for blood sampling. The section 25 of the body 23 pointing away from the inlet aperture is adapted for coupling with a traditional plunger syringe. Such a plunger syringe is used as an aid at the sampling in certain situations, e.g. when the patient, whose blood gas parameters are to be determined, has a very low blood pressure. When the sampling device 2 is placed correctly in the sample container station 1, the measuring chambers 300, 400, 500, and 600 communicate optically with the optical units 30, 40, 50, and 60. The measuring chamber 300 (FIG. 3a) optically communicating with the optical unit 30 is adapted for determination of pH in the blood sample and contains a cellophane membrane 316, to which is immobilized a pH absorbance indicator. When the indicator is in chemical equilibrium with the blood sample, the relation between the acid form of the indicator and the basic form of the indicator reflects the pH-value of the blood sample.

The measuring chamber 400 (FIG. 3b) communicates optically with the optical unit 40 adapted for determination of the carbon dioxide content in the blood sample. This determination takes place on the basis of the transmission properties of the sample for radiation at the wavelength 4260 nm.

The measuring chamber 500 is the measuring chamber wherein the determination of the oxygen content of the sample takes place and this measuring chamber communicates optically with the optical unit 50. At one of its surfaces the measuring chamber 500 has a PVC membrane 501 dyed with the phosphorescent compound PdTFPP (palladium(II)-tetra(pentafluorphenyl)-porphyrin).

The phosphorescent compound is excited with radiation of a wavelength at app. 556 nm, and the oxygen content is determined by determining the characteristics of radiation at the wavelength 673 nm emitted from the excited phosphorescent compound. The chemical and photometric basis for the oxygen determination appears from FIG. 7, 8, and 9 and the description of these. An embodiment of the optical unit 50 appears from FIG. 9 and the description of this.

The measuring chamber 600 (FIG. 3d) is the measuring chamber wherein the hemoglobin content and the oxygen saturation of the blood sample is determined. The measuring chamber is adapted to optically communicate with the optical unit 60 and has a coating of a chemical hemolysis agent on its internal surface. The hemoglobin content in the blood sample is determined by determining characteristics of radiation at the wavelengths 506 nm and 600 nm transmitted through the blood sample.

Finally it appears from FIG. 3 that the sampling device 2 has an integral needle protecting means 26. In the embodiment shown the needle protecting means 26 is a tubular jacket movable in the axial direction of the sampling device between a first position, wherein the jacket exposes the point of the needle, and a second position, wherein the jacket surrounds the point of the needle.

FIG. 3 shows the protecting jacket 26 in the first position, in which it is placed at the sampling moment.

FIG. 4 shows a longitudinal section of the sampling device. The section is placed perpendicular to the section shown in FIG. 3.

The sample container body 23 consists of two halves, of which only one is seen in FIG. 4.

FIG. 5 shows finally the same section as FIG. 3 but in FIG. 5 the protecting jacket is displaced to the second position, wherein it surrounds the point of the needle. The jacket 26 is displaced to this second position immediately after the sampling.

FIG. 6 shows the electrical block diagram for the analyzer 11 and speaks for itself.

Figure 7:
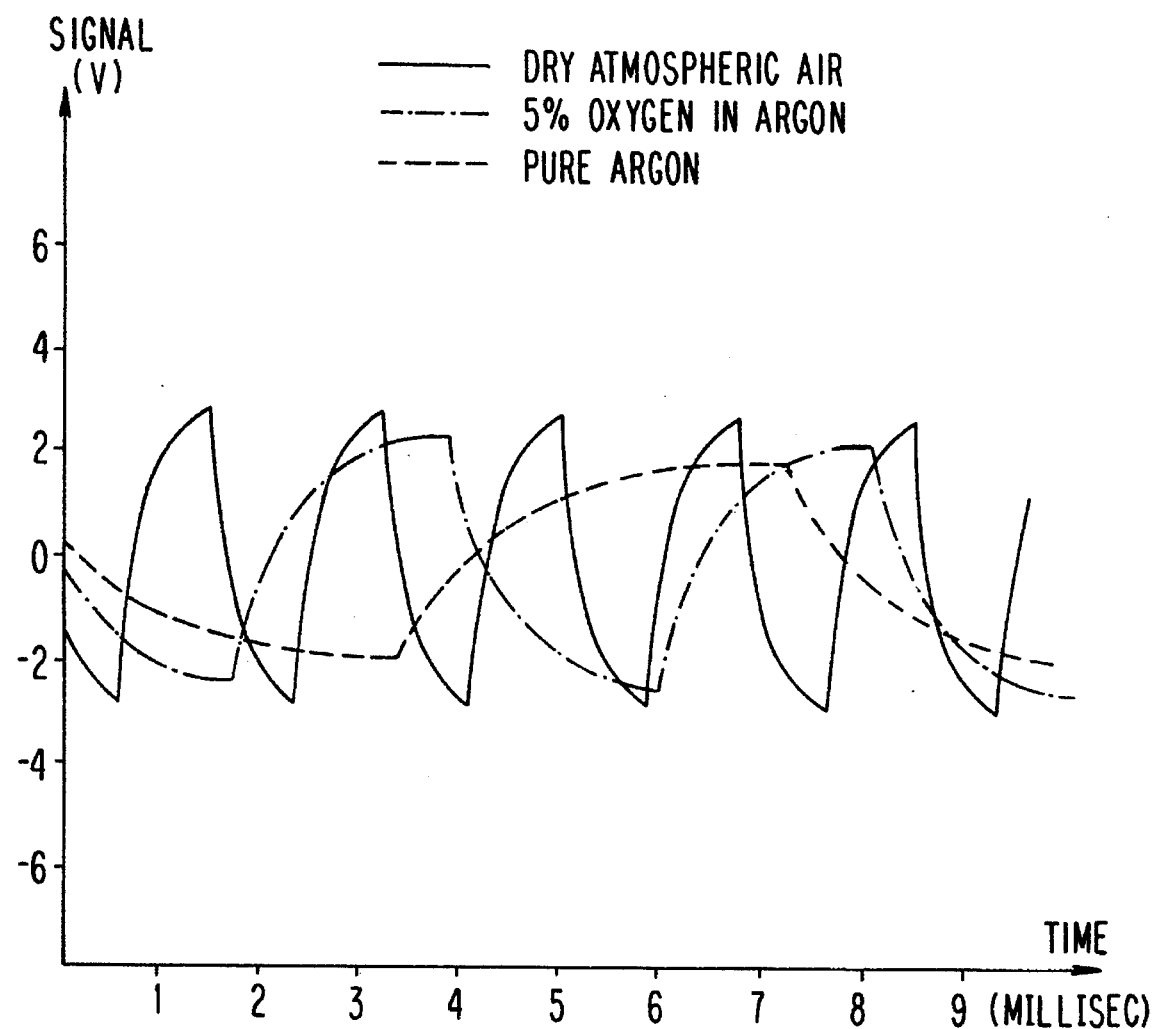
FIG. 7 shows the photometric basis for determination of oxygen.

FIG. 7 shows for each of three different oxygen levels in gaseous samples a signal representing the time-dependent emission radiation from a luminophor excited with a modulated excitation source. It appears from the figure that the frequency of the signal depends on the oxygen level. The figure is provided by use of the sample container according to FIG. 8 and the optical unit according to FIG. 9 with electronics as shown in FIG. 10 and an oscilloscope coupled thereto.

Figure 8:
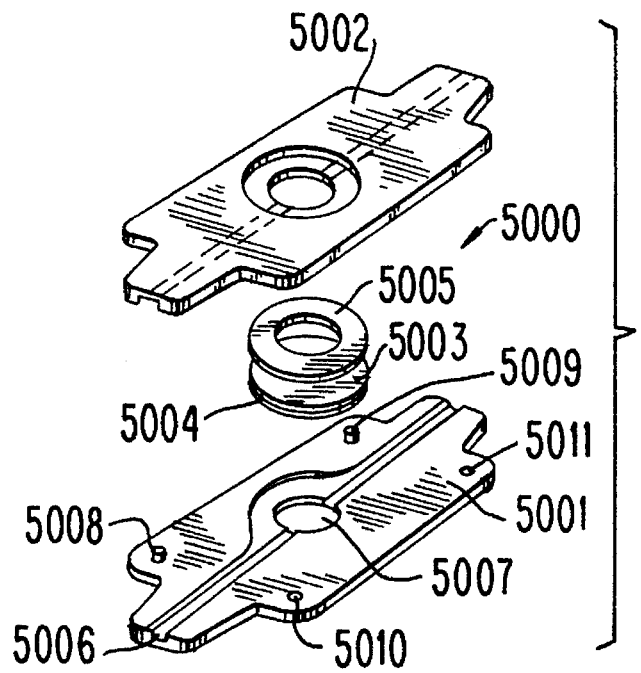
FIG. 8 is a perspective view of a sample container for use in determining oxygen.

FIG. 8 shows a sample container for use in the determination of the oxygen content in a blood sample. The sample container, generally designated 5000, is intended to interact with an analyzer with an optical unit as the one described below in connection with FIG. 9. The sample container 5000 consists of two halves designated 5001 and 5002, respectively. The two halves are assembled by pins 5008 and 5009 in the half 5001 engaging corresponding, not shown recesses in the half 5002, while not shown pins in this engage recesses 5010 and 5011 in the half 5001. The two halves are thereafter welded together by ultrasonic welding. After the assembly the sample container has a sample conduit 5006, which centrally expands transversely into a measuring chamber 5007. The two halves 5001 and 5002 are made from a plastic material. One of the walls in the measuring chamber 5007 consists of a glass plate 5003 in the form of a microscope cover glass, on which there is cast a 2 μm coating 5004 of PVC containing PdTFPP. The preparation of the element consisting of the glass plate 5003 and the PVC coating 5004 is more closely described below. A double adhesive ring 5005 secures the plate 5003 to the sample container part 5002.

Preparation of the Wall Element with Luminophor

A solution consisting of 15 mg PdTFPP (synthesized for the applicant for the purpose), 199.5 mg PVC (BREON S 110/10; BP Kemi, Copenhagen, Denmark) and 1.5 ml tetrahydrofuran (LiChrosolv™; Merck, Darmstadt, West Germany) is cast on a rotating microscope cover glass (φ 12 mm) etched by hydrofluoric acid in a dry atmosphere by putting on 10 μl solution as drops. The speed of rotation is 110–120 rotations/sec.

Less than two hours after the casting the wall element is placed at 90° C. in an incubator for 40 minutes, whereby the PdTFPP containing PVC coating is hardened.

The membrane thickness is reproducible and is about 2 μm.

Figure 9:
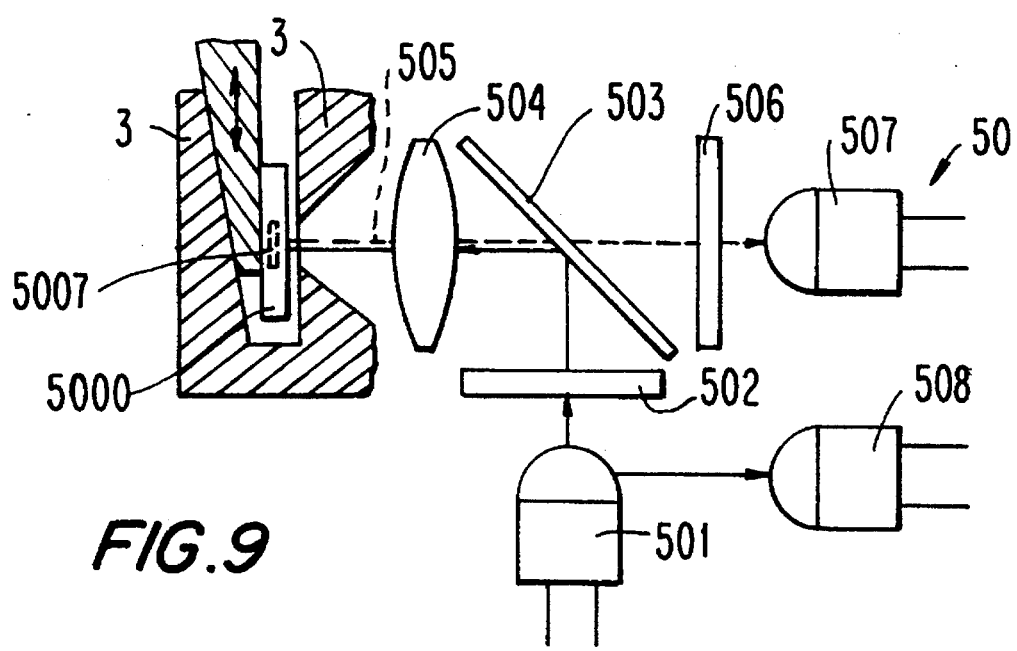
FIG. 9 is a partial cross section of an optical unit in a system according to the invention for photometric determination of oxygen and with a schematic representation of the components forming parts of the optical unit.
Figure 10:
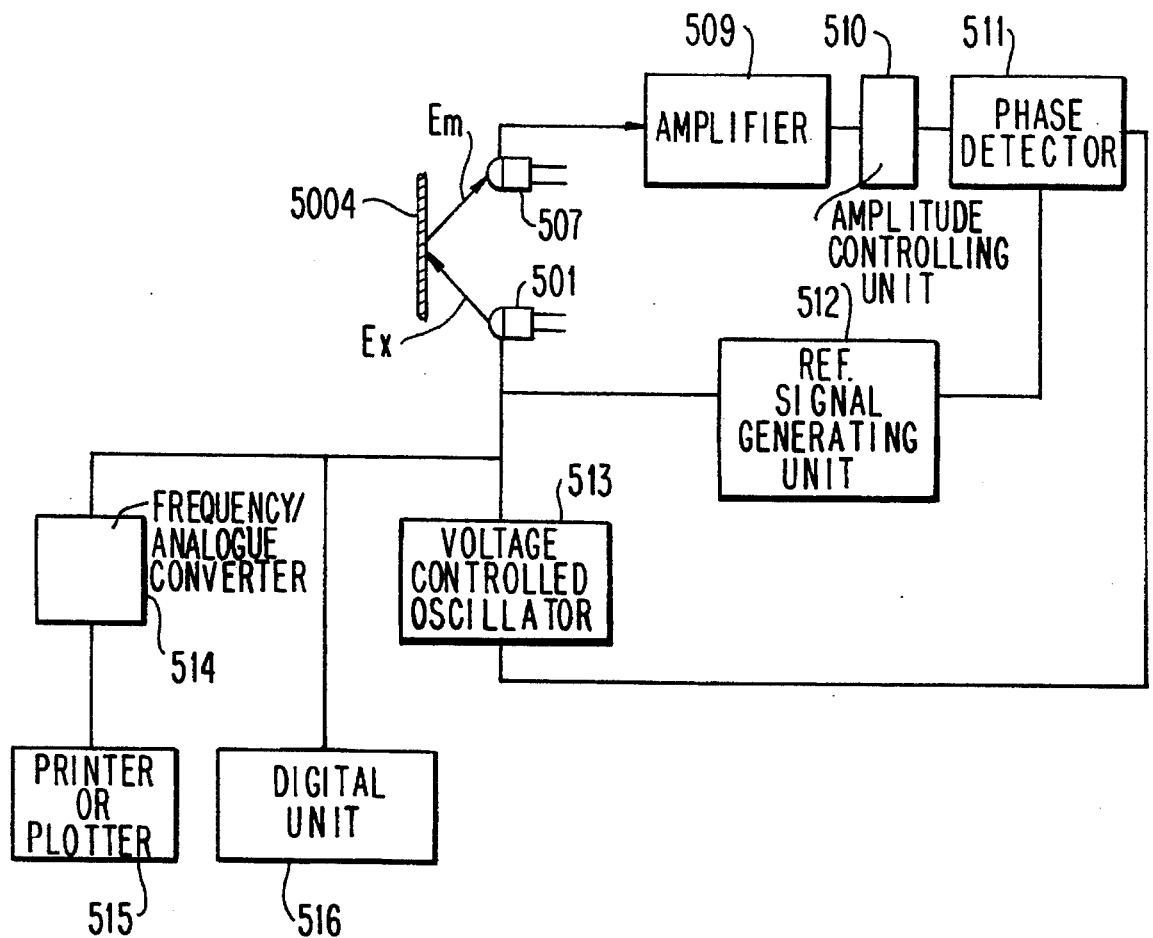
FIG. 10 is a block diagram of the electronic circuit coupled to the optical unit for photometric determination of $O_2$. In the different figures like reference numerals designate like parts.

FIG. 9 shows a prototype of an optical unit 50 for use in determination of oxygen in a blood sample. The blood sample is located in the measuring chamber 5007 in the sample container 5000.

The sample container is placed in a section, generally designated 3.

From a radiation source 501 in the form of a modulated green light diode of the type HBG 5566X from Stanley Electric Co. Ltd, Tokyo, Japan radiation is transmitted through a SWP filter 502 (short wave pass filter), which is specially produced for the applicant for the present purpose, and which eliminates radiation of wavelengths greater than 580 nm. From the filter 502 the radiation is transmitted to a dichroic mirror 503 of the type BSP600 from Optisk Laboratorium, Technical University of Denmark, Lyngby, Denmark. The dichroic mirror 503 reflects radiation at wavelengths less than 600 nm and thereby reflects the radiation from the green light diode. The radiation is reflected from the dichroic mirror to a convex lens 504 (φ 9.9 mm; f 7.3 mm; Thermooptik Arnold GmbH & Co., Weilburg, West Germany). The mutual orientation between the lens 504 and the sample container 5000 is so that the sample container 5000 is situated in the focal plane of the lens. The radiation is focused on the sample container by the lens 504, where it excites a luminophor provided in the measuring chamber 5007. The excited luminophor interacting with the oxygen of the blood sample emits more longwaved radiation 505, which is transmitted from the sample container through the lens 504 and the dichroic mirror 503 to an edge filter 506 of the type RG665 from Schott, Mainz, West Germany. The filter transmits radiation of wavelengths greater than 665 nm. The radiation transmitted through the filter 506 falls onto a silicon photodiode 507 of the type SFH 216 from Siemens, Munich, West Germany, and the photodiode emits a time dependent electrical signal representing the actual luminescence radiation intensity. In FIG. 9 is finally shown a silicon photodiode 508 of the same type as the photodiode 507. The purpose of this photodiode is to determine where in its modulation cycle the radiation source 501 is at a certain moment.

By excitation of a luminophor with a sinus modulated excitation radiation the following equation applies for a luminophor undergoing monoexponential decay:

$$\omega \cdot \tau = \tan \phi$$

where $\omega$ is the angular frequency of the excitation radiation, $\tau$ is the life time of the emission radiation, and $\phi$ is the phase shift of the emission radiation. If the phase shift between the emission radiation and the excitation radiation is electronically maintained at 45° ($\tan_e=1$) applies:

$$\omega = 1/\tau$$

and thus, according to the well-known Stern-Volmer equation:

$$\omega/\omega_0 = 1 + K_{sv} \cdot [O_2]$$

where $\omega_0$ is the angular frequency of the excitation radiation at an oxygen concentration of 0, $K_{sv}$ is the so-called Stern-Volmer constant and $[O_2]$ is the oxygen concentration.

For known values of $\omega_0$ and $K_{sv}$ the oxygen content $[O_2]$ can thus be determined on the basis of detecting the angular frequency $\omega$ or the frequency $f=\omega/2\pi$ of the excitation radiation. In practice the decay is not mono-exponential and a linear relation between $\omega$ (or f) and $[O_2]$ is therefore not seen. A reproducible relation has, however, appeared obtainable not just for sinus modulated excitation radiation, but also for excitation radiation modulated in other ways, i.e. square wave modulated excitation radiation.

A simple electronic circuit whereby $\omega$ or f can be determined is shown in FIG. 10.

FIG. 10 shows the electronic circuit coupled to the optical unit, which circuit in a simple way makes it possible to determine the modulation frequency providing a phase shift of 45° between excitation radiation and emission radiation.

A photodiode 501 is supplied from a voltage controlled oscillator 513 with a time modulated voltage signal. The photodiode 501 consequently emits time modulated radiation, which excites the luminophor in the luminophor containing PVC coating 5004. Subsequently the luminophor emits time modulated emission radiation, which is phase shifted in relation to the excitation radiation. The emission radiation falls onto the photodiode 507 emitting a time modulated current signal which is amplified with a constant quantity in an amplifier 509. The amplified signal is further amplified to a specified amplitude in an amplitude controlling unit 510. In a phase detector 511 the phase of the signal from the unit 510 is compared to the phase of a reference signal, which is phase shifted 45° in relation to the time modulated voltage signal supplying the photodiode 501. The reference signal is generated in a unit 512. The phase detector 511 emits a signal controlling the voltage controlled oscillator 513. By means of the control signal the voltage controlled oscillator 513 is adjusted to such a frequency, that the emission radiation—and with this the input signal to the phase detector 511 from the unit 510—and the reference signal has the same phase. In other words, the voltage controlled oscillator 513 is adjusted to such a frequency that the emission radiation is phase shifted 45° in relation to the excitation radiation.

The frequency of the output signal from the voltage controlled oscillator 513 is registered and transformed to a digital quantity in the unit 516 and/or transformed in a frequency/analog converter 514 to a signal registered by a printer or plotter 515.

In FIG. 10 the photometric system is for clearness represented only by the photodiodes 501 and 507. The other not shown components appear from FIG. 9.

It should be noted that although the determination of the oxygen content via a determination of the frequency of the excitations radiation at a fixed phase shift is only described for a phase shift of 45°, an oxygen determination is obtainable in a similar manner at any other fixed phase shift.

With respect to the dimensions of the sampling device, it is noted that the measuring chamber for oxygen preferably has a volume of 1–50 μl, more preferably 5–25 μ, and in particular 7–12 μl.

We claim:

1. A method for the photometric in vitro determination of the content of oxygen in a blood sample, comprising:
   (a) transferring the blood sample to a sample container:
      (i) having an inlet opening and otherwise being essentially sealed; and
      (ii) incorporating a luminophor in a polymer matrix, whose luminescence is quenched in the presence of oxygen;
   (b) disposing the sample container in optical communication with an optical system comprising a radiation source and a radiation detector for detecting radiation transmitted from said source;
   (c) transmitting radiation from the radiation source to the sample container to excite the luminophor;
   (d) transmitting the luminescence emitted by the excited luminophor to the radiation detector; and
   (e) detecting and registering the luminescence.

2. A sample container for the photometric in vitro determination of the oxygen content in a blood sample, said sample container:
   (a) having an inlet opening and otherwise being essentially sealed; and
   (b) incorporating a luminophor in a polymer matrix whose luminescence is quenched in the presence of oxygen.

3. The sample container according to claim 2, wherein the polymer matrix forms a coating on a portion of the container.

4. The sample container according to claim 2, wherein the polymer matrix is cellulose acetate, polyurethane, polycarbonate/silicone copolymer, or hard polyvinyl chloride, and the luminophor is selected from among those porphyrin compounds which, when incorporated in the polymer matrix, provide a luminescence characteristic of a sufficient size variation allowing the actual oxygen partial pressure to be determined, as long as the ambient oxygen partial pressure varies within the physiological range of up to about 800 mm Hg.

5. The sample container according to claim 4, wherein the polymer matrix is polyvinyl chloride and the luminophor is arylsubstituted tetrabenzoporphyrin.

6. The sample container according to claim 5, wherein the polymer matrix is polyvinyl chloride and the luminophor is a palladium porphyrin.

7. The sample container according to claim 6, wherein the palladium porphyrin is selected from the group consisting of palladium(II)-tetraphenyl porphyrin (PdTPP) and palladium(II-tetra-(pentafluorophenyl)-porphyrin (PdTFPP).

8. The sample container according to claim 7, wherein the luminophor is palladium(II)-tetraphenyl porphyrin (PdTPP).

9. The sample container according to claim 7, wherein the luminophor is palladium(II-tetra-pentafluorophenyl)porphyrin (PdTFPP).

10. A system for the photometric in vitro determination of the content of oxygen in a blood sample, comprising:
    (a) a sample container;
       (i) having an inlet opening and otherwise being essentially sealed; and
       (ii) incorporating a luminophor in a polymer matrix, whose luminescence is quenched in the presence of oxygen; and
    (b) an analyzer;
       (i) having an optical system incorporating a radiation source and a radiation detector for detecting radiation transmitted from the radiation source;

(ii) incorporating means for providing optical communication between the optical system and the sample container so that radiation transmitted from the radiation source is transmitted to the sample container such that the luminophor is excited and the luminescence emitted by the excited luminophor is transmitted to and detected by the radiation detector; and (iii) incorporating means for measuring the luminescence detected by the radiation detector.

11. The system according to claim 10, wherein the luminophor in the polymer matrix forms a coating on a portion of the sample container.

12. The system according to claim 11, wherein the polymer matrix is cellulose acetate, polyurethane, polycarbonate/silicone copolymer, or hard polyvinyl chloride, and the luminophor is selected from among those porphyrin compounds which, when incorporated in the polymer matrix, provide a luminescence characteristic of a sufficient size variation allowing the actual oxygen partial pressure to be determined, as long as the ambient oxygen partial pressure varies within the physiological range of up to about 800 mm Hg.

13. The system according to claim 12, wherein the polymer matrix is polyvinyl chloride and the luminophor is arylsubstituted tetrabenzoporphyrin.

14. The system according to claim 12, wherein the polymer matrix is polyvinyl chloride and the luminophor is a palladium porphyrin.

15. The system according to claim 14, wherein the palladium porphyrin is selected from the group consisting of palladium(II)-tetraphenyl porphyrin (PdTPP) and palladium(II-tetra-(pentafluorophenyl)-porphyrin (PdTFPP).

16. The system according to claim 15, wherein the luminophor is palladium(II)-tetraphenyl porphyrin (PdTPP).

17. The system according to claim 15, wherein the luminophor is palladium(II-tetra-pentafluorophenyl)-porphyrin (PdTFPP).

* * * * *